United States Patent [19]

Sato

[11] 4,177,122

[45] Dec. 4, 1979

[54] PHOTOPOLYMERIZABLE HYDROXY-BENZOPHENONE DERIVATIVE COMPOUNDS AND PHOTOCURABLE COMPOSITIONS

[75] Inventor: Kozi Sato, Tokyo, Japan

[73] Assignee: Toyo Ink Manufacturing Co., Ltd., Tokyo, Japan

[21] Appl. No.: 970,902

[22] Filed: Dec. 19, 1978

[30] Foreign Application Priority Data

Jan. 13, 1978 [JP] Japan ..................................... 53-2037

[51] Int. Cl.² ............................ C08F 2/46; C08F 8/00
[52] U.S. Cl. ......................... 204/159.16; 204/159.14; 204/159.15; 204/159.18; 204/159.23; 427/54.1; 428/413; 428/463; 428/514; 560/209; 560/221
[58] Field of Search ................................ 560/221, 209; 204/159.14, 159.15, 159.18, 159.16, 159.17, 159.23; 96/115 P

[56] References Cited

U.S. PATENT DOCUMENTS

| | | | |
|---|---|---|---|
| 3,341,493 | 9/1967 | Goldberg et al. | 560/221 X |
| 3,365,421 | 1/1968 | Horton | 560/221 X |
| 3,429,852 | 2/1969 | Skoultchi et al. | 560/221 X |
| 3,708,524 | 1/1973 | Murayama et al. | 260/486 B |
| 3,810,938 | 5/1974 | Schmitt et al. | 260/486 R |
| 4,008,138 | 2/1977 | Rosen et al. | 204/159.14 |
| 4,028,204 | 6/1977 | Rosen et al. | 204/159.14 |

*Primary Examiner*—Richard B. Turer
*Attorney, Agent, or Firm*—Frank J. Jordan

[57] ABSTRACT

A process for preparing photopolymerizable photosensitizing compounds which comprises addition reacting a specific benzophenone derivative with an alkylene oxide to obtain a hydroxyl group-containing reaction product which is then esterified with an unsaturated carboxylic acid or addition reacted with glycidyl acrylate; the photopolymerizable photosensitizing compounds; and photocurable compositions comprising the photopolymerizable photosensitizing compound.

10 Claims, No Drawings

PHOTOPOLYMERIZABLE HYDROXY-BENZOPHENONE DERIVATIVE COMPOUNDS AND PHOTOCURABLE COMPOSITIONS

This invention relates to a process for preparing photopolymerizable photosensitizing compounds having built-in sensitizers and to the photopolymerizable photosensitizing compounds so prepared. It also relates to photocurable compositions particularly for printing inks and coating materials, comprising the photopolymerizable photosensitizing compound.

With the recent progress of printing techniques, a high printing speed has been required in the practice of printing. Inks which may be dried instantaneously without being attended with evaporation of solvents have thus been demanded in the printing industrial field, and ultraviolet light curable printing inks began to be marketed. In general, ultraviolet light curable inks now marketed consist mainly of polymerizable prepolymers and monomers as well as photosensitizers and pigments. However, benzoin and benzophenone derivatives used as the photosensitizers in the marketed printing inks decrease in photosensitizability particularly due to the light interception of the pigments contained therein. To overcome this disadvantage at the present time, not only printing inks but also other resinous coating materials contain an excessive amount of a photosensitizer thereby enabling them to be photocured at a desired photocuring speed when used (the amount of a photosensitizer contained in these conventional inks or coating materials being in the range of 5–25% by weight). When such links or coating materials containing a large proportion of the sensitizer are printed on a substrate with a printer, they will swell the rolls and blankets of the printer thereby to cause, for example, non-uniform transfer of the ink or coating material, printing out of register, doubling of dots and scumming of the resulting printed matter due to difficulties in adjustment of pressure of the rolls. In the present-time metallic decorating system, a metalic sheet is printed with a photocurable ink, dried by radiation with a high pressure mercury lamp, coated with an overcoating varnish to increase the gloss of the printed sheet and protect the ink film formed thereon, and then heated to be dried; when such a photocurable ink containing a conventional photosensitizer is printed on a substrate and heated, the resulting ink film will evaporate the photosensitizer therefrom whereby it decreases in weight. This raises a problem as to, for example, the weakening of the ink printed on the substrate.

As a compound for use as eliminating the aforesaid disadvantage, Japanese patent application Laying-Open Gazette No. 61460/73 discloses a compound prepared by reacting a carboxyl group-containing benzophenone derivative with a hydroxyl group-containing ethylenically unsaturated ester. The compound so disclosed, however, is not satisfactory in autophotosensitization and polymerizability.

In addition, U.S. Pat. No. 3,429,852 discloses an adduct of carboxybenzophenone or hydroxybenzophenone with glycidyl (meth)acrylate. Since secondary OH groups are necessarily produced in a reaction for the production of said adduct, offset inks and the like containing such an adduct are disadvantageous from the view-point of printability, in that they will produce printed matter with scums and the like when printed on a substrate.

It has been found that the aforesaid disadvantages may be overcome by using a photopolymerizable photosensitizing compound having built-in sensitizers.

An object of this invention is to provide a process for the preparation of a novel, sensitizer built-in type photopolymerizable photosenitizing compound for photocurable resin compositions.

Another object is to provide the novel photopolymerizable photosensitizing compound.

A still another object is to provide a photocurable resin composition containing the novel photopolymerizable photosensitizing compound.

The process of this invention comprises the steps of: addition reacting a benzophenone derivative represented by the general formula (I)

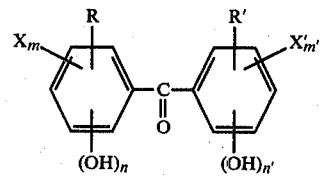

wherein R and R' is an alkyl or alkoxy group having 1–20 carbon atoms, n is an integer of 1–3, n' is an integer of 0–3, X and X' are each a halogen atom, and m and m' are each an integer of 0–3, with an alkylene oxide to obtain a hydroxyl group-containing reaction product, and esterifying the thus obtained hydroxyl group-containing reaction product with an unsaturated carboxylic acid or addition reacting said hydroxyl group-containing reaction product with glycidyl acrylate (or acryl glycidyl ester) to obtain a photopolymerizable photosensitizing compound.

The benzophenone derivatives of the aforesaid general formula include 2-hydroxybenzophenone, 2-hydroxy-4-alkylbenzophenones, 2-hydroxy-4-alkoxybenzophenones, 2,2'-dihydroxybenzophenone, 2,4-dihydroxybenzophenone, 2,2'-dihydroxy-4-alkylbenzophenones, 2,2'-dihydroxy-4-alkoxybenzophenones, 2,2'-dihydroxy-4,4'-dialkylbenzophenones, 2,2',6-trihydroxybenzophenone and 2,2',6,6'-tetrahydroxybenzophenone.

The alkylene oxides used herein include ethylene oxide and propylene oxide.

The unsaturated carboxylic acids used herein include acrylic acid, methacrylic acid, sorbic acid, itaconic acid, crotonic acid, vinylacetic acid and cinnamic acid.

The addition reaction of the benzophenone derivative with the alkylene oxide is effected at a temperature of 80°–160° C. for about one hour usually in the presence of an alkali catalyst such as sodium hydroxide. In this case, it is preferable that the amount of alkylene oxide added to one mol of the benzophenone derivative be in the range of 1–10 mol. More than 10 mol of alkylene oxide added will result in the production of a product having inferior photocurability and, when such a product be used in offset printing inks, it will be easily emulsified thereby to cause scumming of the printing inks, degradation of viscoelasticity thereof, and the like. The esterification between the benzophenone derivative-alkylene oxide adduct and an unsaturated carboxylic acid is effected by the use of a usual method, and it is preferable that this esterification be carried out at such a temperature, such as preferably 80°–120° C., that the unsaturated groups do not cause thermal polymerization and in the presence of an acidic catalyst such as p-toluenesulfonic acid. In this esterification, it is preferable that the adduct be reacted with the unsaturated carboxylic acid in a ratio of from 1.2:1 to 1:1.2 between the OH groups of the adduct and the COOH groups of the carboxylic acid, and that a 60-100% esterification be attained.

In addition, the addition reaction of said benzophenone derivative-alkylene oxide adduct with glycidyl acrylate may preferably be effected at such a temperature (preferably 60°-100° C.) that the unsaturated groups do not cause thermal polymerization and in the presence of a catalyst or a thermal polymerization inhibitor. The catalysts used herein include tetramethyl ammonium salt and lithium acetate, and the polymerization inhibitors used herein include hydroquinone and p-methoxyphenol.

The photopolymerizable photosensitizing compounds having built-in sensitizers of this invention (hereinafter sometimes referred to as "sensitizer built-in polymerizable compound") may be polymerized singly or jointly with unsaturated group-containing resins and may thereafter be photocured in the absence of sensitizers. Thus, they may be used, without the use of sensitizers, in coating materials, overcoating varnishes, printing inks and the like. In addition, even if a sensitizer be used for photocure, the amount thereof required can be small. The sensitizers which may be used are not limited, but they include benzoine, benzoin methyl ether, benzoin isobutyl ether, benzophenone, 4,4'-bisdiethylaminobenzophenone, p-chlorobenzophenone, amyl-p-dimethylamonobenzoic acid, anthraquinone, thioxanthone, methyl-o-benzoylbenzoic acid, p-diethylaminobenzaldehyde acetophenone and p-diethylaminoacetophenone. The compounds of this invention may be prepared to have any desired viscosity (from 0.5 poise/25° C. to 10000 poise/25° C.) depending on the number of carbon atoms of the alkyl groups and the number of mol of alkylene oxide added, and therefore, they may be used as a photosensitizing photocurable diluent (monomer) when they have lower viscosity while they may be used as a light curable prepolymer when they have higher viscosity. Thus, they may be prepared to have any suitable viscosity depending on the purpose for which they are to be used.

This invention will be better understood by the following Reference examples, Examples and Comparative examples wherein all the parts are by weight unless otherwise specified.

REFERENCE EXAMPLE 1

To a four-necked flask provided with a reflux condenser were added 71.7 parts of Epikote 828 (bisphenol type epoxy resin produced by Shell Chemical Inc.), 28.3 parts of acrylic acid, 0.1 part of hydroquinone and 0.1 part of triethylenediamine to form a mixture which was reacted at 90°-120° C. for 15-20 hours while blowing air into the reaction system, thereby to obtain a resin having an acid value of less than 1.

Using the resin so obtained, an ink was prepared in accordance with the following formulation:

| Composition of Ink | | |
|---|---|---|
| Carmine 6BT (produced by Toyo Ink Manufacturing Co., Ltd. | 17.0 Parts | |
| Resin (obtained in this Reference example) | 51.0 | " |
| Benzophenone | 10.0 | " |
| 4,4'-bis(diethylamino)benzophenone | 2.0 | " |
| Trimethylolpropane triacrylate | 20.0 | " |
| | 100.0 Parts | |

*[1]Tack value 10.0
*[2]Flow value 16.5

*[1]Tack values are obtained as follows.
An ink to be tested for tack value is mounted on an ink-o-meter and rotated at 400 rpm, a water temperature of 30° C. and a room temperature of 25° C. The ink is tested for tack value one minute after the start of the rotation by the use of the ink-o-meter under the aforesaid conditions.
*[2]Flow values are obtained as follows.
An ink to be tested for flow value is mounted on a spread-o-meter at room temperature (25° C.). The ink is tested for flow value one minute after the start of application of the weight by the use of the spread-o-meter under the aforesaid conditions, and the flow value is expressed in terms of the radius in millimeter of an area over which the ink spreads.

REFERENCE EXAMPLE 2

Using the resin as obtained in Reference example 1, an ink was prepared in accordance with the following formulation.

| Composition of Ink | | |
|---|---|---|
| Carmine 6 B(T) | 17.0 Parts | |
| Resin (as obtained in Reference example 1) | 51.0 | " |
| Benzophenone | 10.0 | " |
| Para-diethylaminoacetophenone | 2.0 | " |
| Trimethylolpropane triacrylate | 20.0 | " |
| | 100.0 Parts | |

Tack value 10.0
Flow value 16.4

EXAMPLE 1

376.5 parts of 2,2'-dihydroxy-4-octoxy-4'-chlorobenzophenone and 2.0 parts of sodium hydroxide were introduced into an autoclave provided with a thermometer and a device for feeding nitrogen or an alkyklene oxide. The resulting mixture was agitated while purging the autoclave with nitrogen, heated to 140°-180° C. and then incorporated with 101.2 parts of ethylene oxide gradually introduced at less than 5 Kg/cm$^2$ for effecting a reaction therebetween. After the end of introduction of ethylene oxide, agitation of the reaction mixture was continued until a pressure of less than 0.1 Kg/cm$^2$G was reached in the autoclave. Thus, it took 50 minutes to complete the reaction and the resulting reaction product was a viscous adduct of 2,2'-dihydroxy-4-octoxy-4'-chlorobenzophenone with ethylene oxide. The number of mol of ethylene oxide added was 1.15 per hydroxyl group of the benzophenone derivative. Then, 76.9 parts of the adduct so obtained, 23.1 parts of acrylic acid, 0.1 part of hydroquinone, 1.0 part of p-toluenesulfonic acid and 10.0 parts of cyclohexane were introduced into a four-necked flask provided with a reflux condenser and an agitator, to form a mixture which was reacted at 80°-100° C., under reflux of the cyclohexane for 15 hours while blowing air into .the flask. The reaction mixture obtained at this point had an acid value of 6.0 and was heated to 95°-105° C. for 2 hours to remove the cyclohexane therefrom thereby obtaining a reaction product having a viscosity of 45 poise at 25° C. Using the thus obtained product which was a sensitizer built-in polymerizable compound of this invention, an ink was prepared in accordance with the following formulation.

| Composition of Ink | |
|---|---|
| Carmine 6 B(T) | 17.0 Parts |
| Resin as obtained in Reference example 1 | 55.0 " |
| Polymerizable compound of this invention as obtained in Example 1 | 15.0 " |
| Trimethylolpropane triacrylate | 13.0 " |
| | 100.0 Parts |
| Tack value 10.0 | |
| Flow value 16.5 | |

EXAMPLE 2

An autoclave provided with a thermometer and a device for feeding nitrogen and an alkylene oxide was charged with 536 parts of 2,2'-dihydroxy-4,4'-dioctadecylbenzophenone and 1.7 parts of sodium hydroxide and purged with nitrogen while agitating the resulting mixture. The mixture was heated to 130°–160° C. and incorporated slowly with 98.6 parts of ethylene oxide for effecting a reaction therebetween. After the end of the incorporation, the agitation was continued until a pressure of less than 0.1 Kg/cm$^2$G was reached in the autoclave; it took 30 minutes to complete the reaction. There was thus obtained a viscous product which was an adduct of ethylene oxide to 2,2'-dihydroxy-4,4'-dioctadecylbenzophenone. The amount in mol of the ethylene oxide added is 1.12 per hydroxyl group of the benzophenone derivative. Then, 81.5 parts of the adduct so obtained, 18.5 parts of acrylic acid, 0.1 part of hydroquinone, 1.0 part of p-toluenesulfonic acid and 10.0 parts of cyclohexane were reacted together at 80°–100° C. for 10 hours under reflux of the cyclohexane in a four-necked flask fitted with a reflux condenser and an agitator while blowing air into the autoclave. The reaction mixture obtained at this point had an acid value of 5.0 and was heated to 95°–105° C. for 2 hours to be freed of the cyclohexane thereby obtaining a liquid product having a viscosity of 1.2 poise at 25° C. This product (a sensitizer built-in monomer) was low in vicosity and used as the diluent in preparing an ink in accordance with the following formulaton.

| Composition of Ink | |
|---|---|
| Carmine 6 B(T) | 17.0 Parts |
| Resin as obtained in Reference example 1 | 58.0 " |
| 4,4'-bis(diethylamino)benzophenone | 2.0 " |
| Sensitizer built-in monomer as obtained in Example 2 | 23.0 " |
| | 100.0 Parts |
| Tack value 10.0 | |
| Flow value 16.5 | |

EXAMPLE 3

Two hundred and fourteen (214.0) parts of 2,4-dihydroxybenzophenone and 2.3 parts of sodium hydroxide were introduced into an autoclave provided with a thermometer and a device for feeding nitrogen and an alkylene oxide, while purging the autoclave with nitrogen. The resulting mixture in the autoclave was heated to 150°–160° C. and incorporated slowly with 862.4 parts of ethylene oxide under a pressure of less than 5 Kg/cm$^2$ for effecting a reaction therebetween. After the completion of incorporation of the ethylene oxide, the whole continued to be agitated until a pressure of less than 0.1 Kg/cm$^2$G was reached in the autoclave; the reaction took 1.5 hours. There was thus obtained a viscous product which was an adduct of ethylene oxide to 2,4-dihydroxybenzophenone. The average number of mol of the ethylene oxide added per hydroxyl group of the benzophenone derivative was 9.8. Then, 86.5 parts of the thus obtained adduct, 13.5 parts of methacrylic acid, 0.1 part of hydroquinone, 1.0 part of p-toluenesulfonic acid and 10.0 parts of cyclohexane were introduced into a four-necked flask provided with a reflux condenser and an agitator, to form a mixture which was reacted at 80°–100° C. under reflux of the cyclohexane for 12 hours while blowing air into the autoclave. The reaction mixture obtained at this point had an acid value of 5.5 and was freed from the cyclohexane at 95°–105° C. for 2 hours thereby to obtain a liquid product having a viscosity of 1.5 poise at 25° C. This product (sensitizer built-in monomer) had a low viscosity and it was therefore used as the diluent in preparing an ink in accordance with the following fomulation.

| Composition of Ink | |
|---|---|
| Carmine 6 B(T) | 17.0 Parts |
| Resin as obtained in Reference example 1 | 56.0 " |
| Para-diethylaminobenzaldehyde | 2.0 " |
| Sensitizer built-in monomer as obtained in Example 3 | 25.0 " |
| | 100.0 Parts |
| Tack value 10.0 | |
| Flow value 16.8 | |

EXAMPLE 4

Two hundred and twenty-eight (228.0) parts of 2-hydroxy-4-methoxybenzophenone and 1.5 parts of sodium hydroxide were charged into an autoclave provided with a thermometer and a device for feeding nitrogen and an alkylene oxide, to form a mixture which was agitated while purging the autoclave with nitrogen, heated to 130°–160° C. and then incorporated slowly with 50.2 parts of ethylene oxide at a pressure of less than 5 Kg/cm$^2$ to react them together. After the end of the incorporation, the agitation continued until a pressure of less than 0.1 Kg/cm$^2$ was reached in the autoclave; the reaction took 35 minutes to be completed. There was thus obtained a viscous product which was an adduct of ethylene oxide to 2-hydroxy-4-methoxybenzophenone. The number of mole of the ethylene oxide added per hydroxyl group of the benzophenone derivative was 1.14. Then, 81.8 parts of the thus obtained adduct, 18.2 parts of acrylic acid, 0.1 part of hydroquinone, 1.0 part of p-toluenesulfonic acid and 10.0 parts of cyclohexane were reacted together at 80°–100° C. under reflux of the cyclohexane for 13 hours in a four-necked flask fitted with a reflux condenser and an agitator while blowing air into the flask. The reaction mixture obtained at this point had an acid value of 6.0 and was heated to 95°–105° C. for 2 hours to be freed from the cyclohexane thereby obtaining a viscous product having a viscosity of 2575 poise at 25° C. This product (sensitizer built-in prepolymer) had a high viscosity and it was therefore used as the prepolymer in preparing an ink in accordance with the following formulation.

| Composition of Ink | |
|---|---|
| Carmine 6B(T) | 17.0 Parts |
| Sensitizer built-in prepolymer as obtained in Example 4 | 56.0 " |

-continued

| Composition of Ink | | |
|---|---|---|
| Amylparadimethylaminobenzoic acid | 2.0 | " |
| Trimethylolpropane triacrylate | 25.0 | " |
| Tack value 10.0 | | |
| Flow value 16.0 | | |

EXAMPLE 5

Two hundred and fourteen (214.0) parts of 2,2'-dihydroxybenzophenone and 1.5 parts of sodium hydroxide were introduced into a small-sized autoclave provided with a thermometer and a device for feeding nitrogen and an alkylene oxide, to form a mixture which was agitated while purging the autoclave with nitrogen, heated to 130°–150° C. and then incorporated slowly with 133.4 parts of propylene oxide at a pressure of less than 5 Kg/cm$^2$ to react them together. After the end of the incorporation, the whole was agitated until a pressure of less than 0.1 Kg/cm$^2$G was reached in the autoclave; the reaction lasted for 50 minutes. There was thus obtained a viscous product which was an adduct of propylene oxide to 2,2'-dihydroxybenzophenone. The amount of the propylene oxide added per hydroxyl group of the benzophenone derivative was 1.15 mol. Then, 57.6 parts of the thus obtained adduct, 42.4 parts of glycidyl acrylate, 2.0 parts of tetramethylammonium chloride and 0.1 part of hydroquinone were reacted together at 70°–80° C. for 3 hours in a four-necked flask provided with an agitator while blowing air into the autoclave. This reaction ended when the hydroxyl group value of the reaction mixture reached 6.5. The desired product obtained from the reaction mixture had a viscosity of 1565 poise at 25° C. This product (having built-in sensitizers) had a high viscosity and it was therefore used as the prepolymer in preparing an ink in accordance with the following formulation.

| Composition of Ink | | |
|---|---|---|
| Carmine 6B(T) | 17.0 | Parts |
| Sensitizer built-in prepolymer as obtained in Example 5 | 58.0 | " |
| 4,4'-bis(diethylamino)benzophenone | 2.0 | " |
| Sensitizer built-in monomer as obtained in Example 2 | 23.0 | " |
| | 100.0 | Parts |
| Tack value 10.0 | | |
| Flow value 17.0 | | |

EXAMPLE 6

Two hundred and thirty (230.0) parts of 2,2',6-trihydroxybenzophenone and 1.7 parts of sodium hydroxide were introduced into a small-sized autoclave provided with a thermometer and a device for feeding nitrogen and an alkylene oxide, to form a mixture which was agitated while purging the autoclave with nitrogen, heated to 135°–160° C. and then incorporated slowly with 155.8 parts of ethylene oxide at a pressure of less than 5 Kg/cm$^2$. After the end of the incorporation of the ethylene oxide, the whole continued to be agitated until a pressure of less than 0.1 Kg/cm$^2$G was reached in the autoclave, and the reaction time needed was 40 minutes. There was thus obtained a viscous product which was found to be an adduct of ethylene oxide to 2,2',6-trihydroxybenzophenone. The amount of the ethylene oxide added per hydroxyl group of the benzophenone derivative was 1.18 mol. Then, 64.1 parts of the thus obtained adduct, 35.9 parts of acrylic acid, 0.1 part of hydroquinone, 1.0 part of p-toluenesulfonic acid and 10.0 parts of cyclohexane were reacted together at 80°–100° C. under reflux of the cyclohexane for 14 hours in a four-necked flask provided with a reflux condenser and an agitator while blowing air into the autoclave. The reaction mixture obtained at this point had an acid value of 5.4 and was heated to 95°–105° C. for 2 hours to be freed from the cyclohexane thereby obtaining a product having a viscosity of 1985 poise at 25° C. This product (sensitizer built-in polymerizable compound) had a high viscosity and it was therefore used as the prepolymer in preparing an ink in accordance with the following formulation.

| Composition of Ink | | |
|---|---|---|
| Carmine 6B(T) | 17.0 | Parts |
| Sensitizer built-in prepolymer as obtained in Example 6 | 60.0 | " |
| 4,4'-bis(diethylamino)benzophenone | 2.0 | " |
| Sensitizer built-in monomer as obtained in Example 3 | 21.0 | " |
| | 100.0 | Parts |
| Tack value 10.0 | | |
| Flow value 16.7 | | |

EXAMPLE 7

Two hundred and forty-six (246.0) parts of 2,2',4,4'-tetrahydroxybenzophenone and 2.2 parts of sodium hydroxide were charged into a small-sized autoclave provided with a thermometer and a device for feeding nitrogen and an alkylene oxide, to form a mixture which was agitated while purging the autoclave with nitrogen, heated to 140°–160° C. and then incorporated slowly with 207.7 parts of ethylene oxide at a pressure of less than 5 Kg/cm$^2$ to react therewith. After the end of incorporation of the ethylene oxide, the whole continued to be agitated until a pressure of less than 0.1 Kg/cm$^2$G was reached in the autoclave, and the reaction time was 50 minutes. There was thus obtained a viscous product which was an adduct of ethylene oxide to 2,2',4,4'-tetrahydroxybenzophenone. The amount of the ethylene oxide added was 1.18 mol per hydroxyl group of the benzophenone derivative. Then, 61.2 parts of the thus obtained adduct, 38.8 parts of acrylic acid, 0.1 part of hydroquinone, 1.0 part of p-toluenesulfonic acid and 10.0 parts of cyclohexane were reacted together at 80°–100° C. under reflux of the cyclohexane for 14 hours in a four-necked flask provided with a reflux condenser and an agitator while blowing air into the autoclave. The reaction mixture obtained at this point had an acid value of 5.8 and was heated to 95°–105° C. for 2 hours to be freed from the cyclohexane. There was thus obtained a product (sensitizer built-in prepolymer) had a viscosity of as high as 2625 poise at 25° C. and was therefore used as the prepolymer in preparing an ink in accordance with the following formulation.

| Composition of Ink | | |
|---|---|---|
| Carmine 6B (T) | 17.0 | Parts |
| Sensitizer built-in prepolymer as obtained in Example 7 | 54.0 | " |
| 4,4'-bis(diethylamino)benzophenone | 2.0 | " |
| Trimethylolpropane triacrylate | 27.0 | " |
| | 100.0 | Parts |

-continued

| Composition of Ink |
|---|
| Tack value 10.0 |
| Flow value 16.8 |

COMPARATIVE EXAMPLE 1

The inks as obtained in Examples 1–7 and those as obtained in Reference examples 1–2 were each placed on a nitrile rubber-made blanket for general oily inks, allowed to stand for 24 hours and then tested for its tendency to swell the blanket.

The results are that the blankets on which the inks as obtained in Reference examples 1–2 were placed were swollen while those on which the inks as obtained in Examples 1–7 exhibited no sign of being swollen.

COMPARATIVE EXAMPLE 2

Red offset printing inks as obtained in Examples 1–7 and those as obtained in Reference examples 1–2 were tested for their tendency to swell the printing rubber rolls and blankets of a printing machine for printing metal sheets by inspecting how many sheets of 10,000 sheets of paper were printed with each of the printing inks without said rolls and blankets being swollen therewith by the use of a printer for metal sheets, operating at 60 rpm. In the test, soon after printed, prints so obtained were placed on a travelling conveyor and passed 10 cm below each of three 8-KW high pressure mercury lamps having an intensity of 80 W/cm to be dried by radiation. The printing inks were thus evaluated as indicated in the following Table 1.

Table 1

|  | *1 Curability of ink | Tendency to swell blankets and | |
|---|---|---|---|
|  |  | Blanket | Printing roller |
| Ink as obtained in Reference example 1 | 100 m/min. | Swollen when 1,000 sheets printed | Swollen when 4,000 sheets printed |
| Ink as obtained in Reference example 2 | 100 " | " | " |
| Ink as obtained in Example 1 | 70 " | Not swollen when 10,000 sheets printed | Not swollen when 10,000 sheets printed |
| Ink as obtained in Example 2 | 100 " | " | " |
| Ink as obtained in Example 3 | 100 " | " | " |
| Ink as obtained in Example 4 | 80 " | " | " |
| Ink as obtained in Example 5 | 80 " | " | " |
| Ink as obtained in Example 6 | 100 " | " | " |
| Ink as obtained in Example 7 | 100 " | " | " |

*1 Travelling velocity of ink required for drying the ink, the drying being determined by finger touch method

COMPARATIVE EXAMPLE 3

The inks as obtained in Reference examples 1–2 and Examples 1–7 were each coated uniformly on a metal sheet by the use of an applicator for coating to a depth of 3 mil and then passed at a conveyor speed of 32 m/min. below the three high pressure mercury lamps in the same manner as in Comparative example 2 to be dried by radiation, thereby to see the weight loss of the ink coated on the metal sheet after having been so dried. The inks so dried were then heated in an oven at 180° C. for 10 minutes to see the weight loss thereof after having been so heated.

The results are shown in the following Table 2.

Table 2

|  | Wt. loss by radiation | Wt. loss by heat |
|---|---|---|
| Ink as obtained in Reference example 1 | 0% | 11.0% |
| Ink as obtained in Reference example 2 | " | 11.5% |
| Ink as obtained in Example 1 | " | 0% |
| Ink as obtained in Example 2 | " | 0% |
| Ink as obtained in Example 3 | " | 0.1% |
| Ink as obtained in Example 4 | " | 2.5% |
| Ink as obtained in Example 5 | " | 0% |
| Ink as obtained in Example 6 | " | 0% |
| Ink as obtained in Example 7 | " | 0% |

Pigments, reactive resins and reactive solvents which may be used together with the sensitizer built-in compounds of the present invention in the preparation of printing inks for example, are illustrated hereinbelow.

The pigments include azo pigments such as Hansa, Yellow, Benzidine Yellow, Lake Red C, Carmine 6B and Permanent Red 2B; phthalocyanine pigments such as phthalocyanine blue and phthalocyanine green; quinacridone pigments; isoindoline pigments; quinophthalon pigments; and other organic pigments and also include carbon black, titanium dioxide, rouge, zinc dioxide, calcium carbonate and other inorganic pigments.

The reactive resins include epoxy (meth)acrylate, alkyd (meth)acrylate, urethane-modified (meth)acrylate, and compounds prepared by reacting cyclopentadiene or dicyclopentadiene with allyl alcohol, butenediol or β-hydroxyethyl acrylate to form a copolymer which is then esterified with (meth)acrylic acid. The terms "(meth)acrylate" and "(meth)acrylic acid" are intended to mean "acrylate and methacrylate" and "acrylic acid or methacrylic acid" respectively throughout the specification.

The reactive solvents include trimethylolpropane (meth)acrylate, pentaerithritol tetra(meth)acrylate, dipentaerithritol (meth)acrylate, dipentaerithritol hexaacrylate, dipentaerithritol pentaacrylate, and compounds prepared by addition reacting a monofunctional or polyfunctional phenolic compound with an alkylene oxide (1–10 mol) and then esterifying the resulting adduct with (meth)acrylic acid. They also include ethylene glycol di(meth)acrylate, diethylene glycol (meth)acrylate, 1,3-butanediol di(meth)acrylate, 1,4-butanediol di(meth)acrylate, 1,6-hexanediol di(meth)acrylate, 2-hydroxyethyl (meth)acrylate, 2-hydroxylpropyl (meth)acrylate, glycidyl (meth)acrylate, triallyl isocyanurate, triallyl citrate, polyethyleneglycol diacrylate, phenylglycidyl acrylate and phenylenediglycol diacrylate. These reactive solvents may be used singly or jointly.

What is claimed is:

1. A process for preparing a photopolymerizable photosensitizing compound comprising the steps of:

addition reacting with an alkylene oxide a benzophenone derivative represented by the following general formula (I)

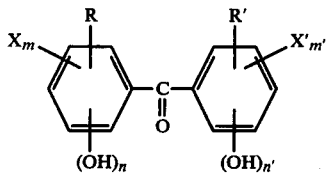

wherein R and R' are an alkyl or alkoxy group having 1 to 20 carbon atoms, n is an integer of 1 to 3, n' is an integer of 0 to 3, X and X' are a halogen atom, and m and m' are an integer of 0 to 3, to obtain a hydroxyl group-containing reaction product and then esterifying the thus obtained reaction product with an unsaturated carboxylic acid to obtain the photopolymerizable photosensitizing compound.

2. A process for preparing a photopolymerizable photosensitizing compound consisting the steps of:

addition reacting with an alkylene oxide a benzophenone derivative represented by the following general formula (I)

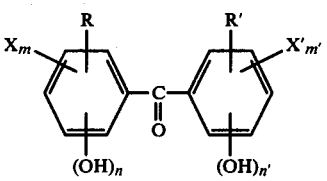

wherein R and R' are an alkyl or alkoxy group having 1 to 20 carbon atoms, n is an integer of 1 to 3, n' is an integer of 0 to 3, X and X' are a halogen group, and m and m' are an integer of 0 to 3, to obtain a hydroxyl group-containing reaction product and then addition reacting the thus obtained reaction product with glycidyl acrylate to obtain the photopolymerizable photosensitizing compound.

3. A process according to claim 1 or 2, wherein the benzophenone derivative is addition reacted with the alkylene oxide in an amount of 1–10 mol thereof per hydroxyl group of the benophenone derivative.

4. A process according to claim 1, wherein the benzophenone derivative is 2-hydroxybenzophenone, a 2-hydroxy-4-alkylbenzophenone, a 2-hydroxy-4-alkoxybenzophenone, 2,2'-dihydroxybenzophenone, 2,4-dihydroxybenzophenone, a 2,2'-dihydroxy-4-alkylbenzophenone, a 2,2'-dihydroxy-4-alkoxybenzophenone, a 2,2'-dihydroxy-4,4'-dialkylbenzophenone, 2,2',6-trihydroxybenzophenone or 2,2',6,6'tetrahydroxybenzophenone.

5. A process according to claim 4, wherein the alkylene oxide is ethylene oxide or propylene oxide and the unsaturated carboxylic acid is acrylic, methacrylic, sorbic, itaconic, crotonic, vinylacetic or cinnamic acid.

6. A process according to claim 2, wherein the benzophenone derivative is 2-hydroxybenzophenone, a 2-hydroxy-4-alkylbenzophenone, a 2-hydroxy-4-alkoxybenzophenone, 2,2'-dihydroxybenzophenone, 2,4-dihydroxybenzophenone, a 2,2'-dihydroxy-4-alkylbenzophenone, a 2,2'-dihydroxy-4-alkoxybenzophenone, a 2,2'-dihydroxy-4,4'-dialkylbenzophenone, 2,2',6-trihydroxybenzophenone or 2,2',6,6'-tetrahydroxybenzophenone.

7. A process according to claim 6, wherein the alkylene oxide is ethylene oxide or propylene oxide.

8. The photopolymerizable photosensitizing compounds prepared by the process of any one of claims 1–2 and 4–7.

9. The photopolymerizable photosensitizing compounds prepared by the process of claim 3.

10. A photocurable composition comprising, by weight, 0.1–80 parts of the photopolymerizable photosensitizing compound of any one of claim 1–2 and 4–7, 0–60 parts of a pigment, 0–80 parts of a reactive resin and 0–50 parts of a reactive solvent.

* * * * *